(12) United States Patent
Turgeman et al.

(10) Patent No.: US 11,701,050 B2
(45) Date of Patent: *Jul. 18, 2023

(54) DATA REUSE FOR FILLING IN MISSING DATA POINTS

(71) Applicant: Biosense Webster (Israel) Ltd., Yokneam (IL)

(72) Inventors: Aharon Turgeman, Zichron Ya'acov (IL); Gal Hayam, Tivon (IL); Tal Haim Bar-on, Kiryat Tivon (IL); Nakdimon Nissim Levy, Pardes Hana (IL); Wagdi Hani Hagla, Julis Village (IL); Shiran Eliyahu, Yokneam Illit (IL); Michael Maydel, Haifa (IL); Alaa Zoubi, Sakhnin (IL); Refael Itah, Tel Aviv (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/571,991

(22) Filed: Jan. 10, 2022

(65) Prior Publication Data
US 2022/0125364 A1 Apr. 28, 2022

Related U.S. Application Data

(63) Continuation of application No. 16/654,600, filed on Oct. 16, 2019, now Pat. No. 11,253,183.

(51) Int. Cl.
*A61B 5/339* (2021.01)
*A61B 5/00* (2006.01)

(52) U.S. Cl.
CPC ............ *A61B 5/339* (2021.01); *A61B 5/7225* (2013.01); *A61B 5/742* (2013.01)

(58) Field of Classification Search
CPC ........ A61B 5/339; A61B 5/7225; A61B 5/742
See application file for complete search history.

(56) References Cited

U.S. PATENT DOCUMENTS

| 5,391,199 A | 2/1995 | Ben-Haim |
|---|---|---|
| 5,443,489 A | 8/1995 | Ben-Haim |

(Continued)

FOREIGN PATENT DOCUMENTS

| CN | 104066368 A | 9/2014 |
|---|---|---|
| EP | 3122246 A1 | 2/2017 |

(Continued)

OTHER PUBLICATIONS

European Search Report for corresponding EPA No. 20201918.8 dated Feb. 10, 2021.

*Primary Examiner* — Catherine M Voorhees
*Assistant Examiner* — Roland Dinga
(74) *Attorney, Agent, or Firm* — Volpe Koenig

(57) ABSTRACT

A medical display processing device and a method of reusing data includes acquiring, over time via electrodes, electrical signals each acquired via one of the electrodes and indicating electrical activity at a location of a portion of patient anatomy in a 3D space. Electrical signal data, corresponding to the electrical signals, is filtered according to first filter parameter settings and first mapping information is generated for displaying a map of the portion of patient anatomy and the filtered electrical signal data. An indication of a region of the portion of patient anatomy on the map is received and second mapping information is generated for displaying, at the region on the map, a portion of the electrical signal data previously filtered from display.

20 Claims, 7 Drawing Sheets

(56) References Cited

U.S. PATENT DOCUMENTS

| | | | |
|---|---|---|---|
| 5,558,091 | A | 9/1996 | Acker et al. |
| 6,172,499 | B1 | 1/2001 | Ashe |
| 6,177,792 | B1 | 1/2001 | Govari et al. |
| 6,266,551 | B1 | 7/2001 | Osadchy et al. |
| 6,690,963 | B2 | 2/2004 | Ben-Haim et al. |
| 6,788,967 | B2 | 9/2004 | Ben-Haim et al. |
| 11,253,183 | B2* | 2/2022 | Turgeman ............... G06T 19/20 |
| 2003/0023130 | A1 | 1/2003 | Ciaccio et al. |
| 2009/0262979 | A1 | 10/2009 | Markowitz et al. |
| 2009/0264727 | A1 | 10/2009 | Markowitz et al. |
| 2013/0274582 | A1 | 10/2013 | Afonso et al. |
| 2017/0092014 | A1 | 3/2017 | Perlman et al. |
| 2019/0053729 | A1 | 2/2019 | Haymam et al. |
| 2019/0099078 | A1* | 4/2019 | Zeidan ............... A61N 1/37247 |

FOREIGN PATENT DOCUMENTS

| | | |
|---|---|---|
| RU | 2011154026 A | 7/2013 |
| WO | 2017/156008 A1 | 9/2017 |

* cited by examiner

EA Points
☐ Respiration Gated
☐ Tissue Proximity N/A
Continuous Mapping          Map: 1-Map
☑ Cycle Length [Range ▼]      ─●─●─────────
☐ Pattern Matching              250  300

610
                                ─────────────○── Threshold
☑ Position Stability           ─────●─────────── mm
☑ LAT Stability                      3
☐ Force                        ────────●──────── ms
☐ Do Not Acquire While Pacing          3
    Density                    [Above Minimum Threshold ⌄]

[1  ▼] mm
FAM
☐ Exclude When Force Is Above Higher Threshold

FIG. 6A

EA Points
☐ Respiration Gated
☐ Tissue Proximity N/A
Continuous Mapping          Map: 1-Map
☑ Cycle Length [Range ▼]      ─●─●─────────
☐ Pattern Matching              250  300

610
                                ─────────────○── Threshold
☑ Position Stability           ●──────────────── mm
☑ LAT Stability                 1
☐ Force                        ────────●──────── ms
☐ Do Not Acquire While Pacing          3
    Density                    [Above Minimum Threshold ⌄]

[1  ▼] mm
FAM
☐ Exclude When Force Is Above Higher Threshold

FIG. 6B

DATA REUSE FOR FILLING IN MISSING DATA POINTS

CROSS REFERENCE TO RELATED APPLICATION

This application is a continuation of U.S. application Ser. No. 16/654,600, which was filed on Oct. 16, 2019, which is incorporated by reference as if fully set forth herein.

FIELD OF INVENTION

The present application relates the field of medical diagnosis and treatment, particularly as it pertains to atrial fibrillation. In particular, the present application relates to systems and methods for determining regions of interest to be ablated for treatment of cardiac arrhythmia, such as atrial fibrillation, and, more particularly, to systems and methods for determining atrial fibrillation regions of interest to be ablated using maps representing detected electrical activity of the heart and maps representing spatio-temporal manifestations of the conditions indicative of the electrical activity of the heart.

BACKGROUND

Medical personnel, such as ear, nose and throat (ENT) physicians and cardiologists, use medical tools for performing medical procedures within patient anatomy. Medical tools, such as catheters, may be used to detect electrical activity in patient anatomy (e.g., electro-cardiogram (ECG) signals of a heart) for generating maps (e.g., high resolution maps) of the anatomy (e.g., map of the heart).

For example, ECG signals of a heart are acquired (i.e., recorded for a period of time, such as 20 to 30 seconds) via a plurality of catheter electrodes placed at different areas of the heart. The acquired signals are monitored and used, along with location information indicating locations of the medical tool and the electrodes in a three dimensional (3D) space, to create the dynamic maps of the heart. Based on a visual assessment of the maps, a region of interest of the heart may be determined, which may include an area of the heart causing an irregular heart rhythm to be targeted for ablation.

SUMMARY

A method of reusing data is provided which improves processing performance of a medical display processing system. The method includes acquiring, over time via a plurality of electrodes, electrical signals, each signal acquired via one of the plurality of electrodes and indicating electrical activity at a location of a portion of patient anatomy in a three dimensional (3D) space. The method also includes filtering electrical signal data, corresponding to the electrical signals, according to a first plurality of filter parameter settings and generating first mapping information for displaying a map of the portion of patient anatomy and the filtered electrical signal data. The method also includes receiving an indication of a region of the portion of patient anatomy on the map and generating, second mapping information for displaying, at the region on the map, a portion of the electrical signal data previously filtered from display.

A medical display processing device which improves processing performance is provided which includes memory configured to store electrical signal data and a processing device. The processing device is configured to receive the electrical signal data, corresponding to electrical signals acquired over time via a plurality of electrodes, each signal indicating electrical activity at a location of a portion of patient anatomy in 3D space. The processing device is also configured to filter the electrical signal data according to a first plurality of filter parameter settings and generate first mapping information for displaying a map of the portion of patient anatomy and the filtered electrical signal data. The processing device is also configured to receive an indication of a region of the portion of patient anatomy on the map and generate, second mapping information for displaying, at the region on the map, a portion of the electrical signal data previously filtered from display.

A medical processing system which improves processing performance is provided which includes a plurality of electrodes each configured to acquire electrical signals over time, each signal indicating electrical activity at a location of a portion of patient anatomy in 3D space. The system also includes a display device configured to display a map of the portion of patient anatomy and electrical signal data corresponding to the electrical signals. The system also includes a processing device configured to receive the electrical signal data and filter the electrical signal data according to a first plurality of filter parameter settings. The processing device is also configured to generate first mapping information for displaying, on the display device, the map of the portion of patient anatomy and the filtered electrical signal data, receive an indication of a region of the portion of patient anatomy on the map and generate, second mapping information for displaying, on the display device at the region on the map, a portion of the electrical signal data previously filtered from the display device.

BRIEF DESCRIPTION OF THE DRAWINGS

A more detailed understanding can be had from the following description, given by way of example in conjunction with the accompanying drawings wherein:

FIG. 6A is an example of displayed filter parameter settings for filtering data displayed in the pulmonary vein regions of the heart shown in FIG. 6C;

FIG. 6B is an example of displayed filter parameter settings for filtering data displayed in a central region of the heart shown in FIG. 6C.

DETAILED DESCRIPTION

Conventional medical procedures for determining regions of interest (e.g., of the heart) to be targeted for ablation are time consuming (e.g., several hours) and rely on medical personnel with specific expertise and experience, (typically requiring many hours of training). To facilitate efficient and accurate determination of these regions of interest from viewing the display, a filter (e.g., a hard filter) is typically used to remove a large amount of data points (e.g., data indicating catheter position, impedance, and tissue proximity indication (TPI) for detecting catheter proximity to the tissue) from the mapping, so that the resulting map is not visually overwhelming to medical personnel (e.g., physician).

In some cases, the medical personnel may wish to view data (e.g., electrical signal data) initially filtered out by the filter. For example, gaps in the electrical signal data can exist for specific regions on the map, such as missing local activation time (LAT) values to achieve a full cycle length (CL) mapping. It is often difficult and time consuming, however, to identify and retrieve data that is filtered out by the hard filter, negatively impacting the medical procedure.

Features of the present disclosure efficiently identify, retrieve and reuse the missing data for display on one or more identified regions of the map, resulting in a more accurate and comprehensive map.

Figure 1:
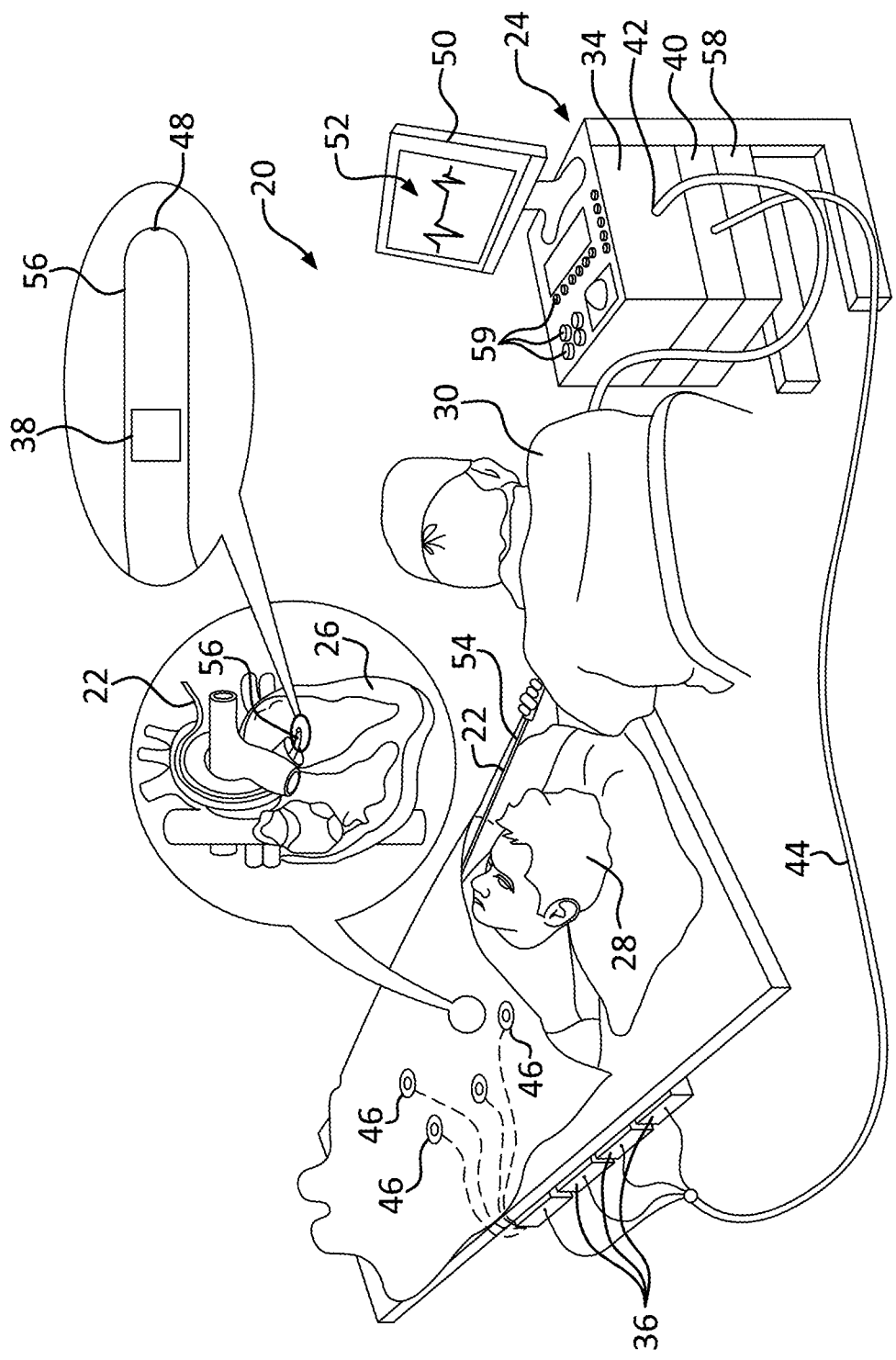
FIG. 1 is an illustration of an example medical system for navigating a tool in 3D space according to embodiments disclosed herein.

Referring now to FIG. 1, an illustration of an example medical system 20 is shown that may be used to generate and display information 52 (e.g., a chart, anatomical models of a portion of a patient and signal information). Tools (i.e., medical tools), such as tool 22, can be any tool used for diagnostic or therapeutic treatment, such as for mapping electrical potentials in a heart 26 of a patient 28. Alternatively, tools may be used, mutatis mutandis, for other therapeutic and/or diagnostic purposes of different portions of anatomy, such as in the heart, lungs or other body organs, such as the ear, nose, and throat (ENT). Tools may include, for example, probes, catheters, cutting tools and suction devices.

An operator 30 may insert the tool 22, via a handle 54, into a portion of patient anatomy, such as the vascular system of the patient 28, so that a tip 56 of the tool 22 enters a chamber of the heart 26. The control console 24 may use magnetic position sensing to determine position coordinates of the tool (e.g., coordinates of the tip 56) in 3D space inside the heart 26. To determine the position coordinates, a driver circuit 34 in the control console 24 may drive, via connector, 44, field generators 36 to generate magnetic fields within the anatomy of the patient 28.

The field generators 36 include one or more emitter coils (not shown in FIG. 1), placed at known positions external to the patient 28, which are configured to generate magnetic fields in a predefined working volume that contains a portion of interest of the patient anatomy. Each of the emitting coils is driven by a different frequency to emit a constant magnetic field in 3D space. For example, in the example medical system 20 shown in FIG. 1, one or more emitter coils can be placed below the torso of the patient 28 and each configured to generate magnetic fields in a predefined working volume that contains the heart 26 of the patient.

As shown in FIG. 1, a magnetic field location sensor 38 is disposed at the tip 56 of tool 22. The magnetic field location sensor 38 is used to determine the position of the receiving coil in 3D space and generate electrical signals based on the amplitude and phase of the magnetic fields. Although the magnetic field location sensor 38 is disposed at the tip 56 of tool 22, a tool can include one or more magnetic field location sensors each disposed at any portion of the tool.

The signals are wirelessly communicated to the control console 24 via a wireless communication interface (e.g., interface 312 shown at FIG. 3) at the tool 22 that may communicate with a corresponding input/output (I/O) interface 42 in the control console 24. The wireless communication interface 312 and the I/O interface 42 may operate in accordance with any suitable wireless communication standard that is known in the art, such as for example, infrared (IR), radio frequency (RF), Bluetooth, one of the IEEE 802.11 family of standards (e.g., Wi-Fi), or the HiperLAN standard. The body surface electrodes 46 may include one or more wireless sensor nodes integrated on a flexible substrate. The one or more wireless sensor nodes may include a wireless transmit/receive unit (WTRU) enabling local digital signal processing, a radio link, and a miniaturized rechargeable battery, as described in more detail below.

The I/O interface 42 may enable the control console 24 to interact with the tool 22, the body surface electrodes 46 and the position sensors (not shown). Based on the electrical impulses received from the body surface electrodes 46 and the electrical signals received from the tool 22 via the I/O interface 42 and other components of medical system 20, the signal processor 40 may determine the location of the tool in 3D space and generate the display information 52, which may be shown on a display 50.

The signal processor 40 is configured to process the signals to determine the position coordinates of the tip 56 in 3D space, including both location and orientation coordinates. The method of position sensing described hereinabove is implemented in the CARTO mapping system produced by Biosense Webster Inc., of Diamond Bar, Calif., and is described in detail in the patents and the patent applications cited herein.

The magnetic field location sensor 38 transmits a signal to the control console 24 which indicates location coordinates of the tool 22 (e.g., location coordinates of the tip 56) in 3D space. The magnetic field location sensor 38 may include one or more miniature receiving coils (e.g., receiving coil(s) 304 shown in FIG. 3) and may include multiple miniature coils oriented along different axes. Alternatively, the magnetic field location sensor 38 may include another type of magnetic sensor or position transducers of other types, such as impedance-based or ultrasonic location sensors. Although FIG. 1 shows the tool 22 having a single location sensor, embodiments may include tools with more than one location sensor. Magnetic position tracking techniques are described, for example, in U.S. Pat. Nos. 5,391,199, 5,443,489, 6,788, 967, 6,690,963, 5,558,091, 6,172,499, 6,177,792, whose disclosures are incorporated herein by reference.

The tool 22 may also include an electrode 48 coupled to the tip 56 and configured to function as an impedance-based position transducer. Additionally or alternatively, the electrode 48 may be configured to measure a certain physiological property, for example the local surface electrical potential (e.g., of cardiac tissue) at one or more locations. The electrode 48 may be configured to apply RF energy to ablate endocardial tissue in the heart 26.

The signal processor 40 may be included in a general-purpose computer, with a suitable front end and interface circuits for receiving signals from the tool 22 and controlling the other components of the control console 24. The signal processor 40 may be programmed, using software, to perform the functions that are described herein. The software may be downloaded to the control console 24 in electronic form, over a network, or it may be provided on non-transitory tangible media, such as optical, magnetic or electronic memory media. Alternatively, some or all of the functions of the signal processor 40 may be performed by dedicated or programmable digital hardware components.

In the example shown at FIG. 1, the control console 24 is connected, via cable 44, to body surface electrodes 46, each of which are attached to patient 28 using patches (e.g., indicated in FIG. 1 as circles around the electrodes 46) that adhere to the skin of the patient. In addition or alternative to the patches, body surface electrodes 46 may also be positioned on the patient using articles worn by patient 28 which include the body surface electrodes 46 and may also include one or more position sensors (not shown) indicating the location of the worn article. For example, body surface electrodes 46 can be embedded in a vest that is configured to be worn by the patient 28. During operation, the body surface electrodes 46 assist in providing a location of the tool (e.g., catheter) in 3D space by detecting electrical impulses generated by the polarization and depolarization of cardiac tissue and transmitting information to the control console 24, via the cable 44. The body surface electrodes 46 can be equipped with magnetic location tracking and can help identify and track the respiration cycle of the patient 28.

Additionally or alternatively, the tool 22, the body surface electrodes 46 and other sensors (not shown) may communicate with the control console 24 and one another via a wireless interface. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions.

During the diagnostic treatment, the signal processor 40 may present the display information 52 and may store data representing the information 52 in a memory 58. The memory 58 may include any suitable volatile and/or non-volatile memory, such as random access memory or a hard disk drive. The operator 30 may be able to manipulate the display information 52 using one or more input devices 59. Alternatively, the medical system 20 may include a second operator that manipulates the control console 24 while the operator 30 manipulates the tool 22. It should be noted that the configuration shown in FIG. 1 is an example. Any suitable configuration of the medical system 20 may be used and implemented.

Figure 2:
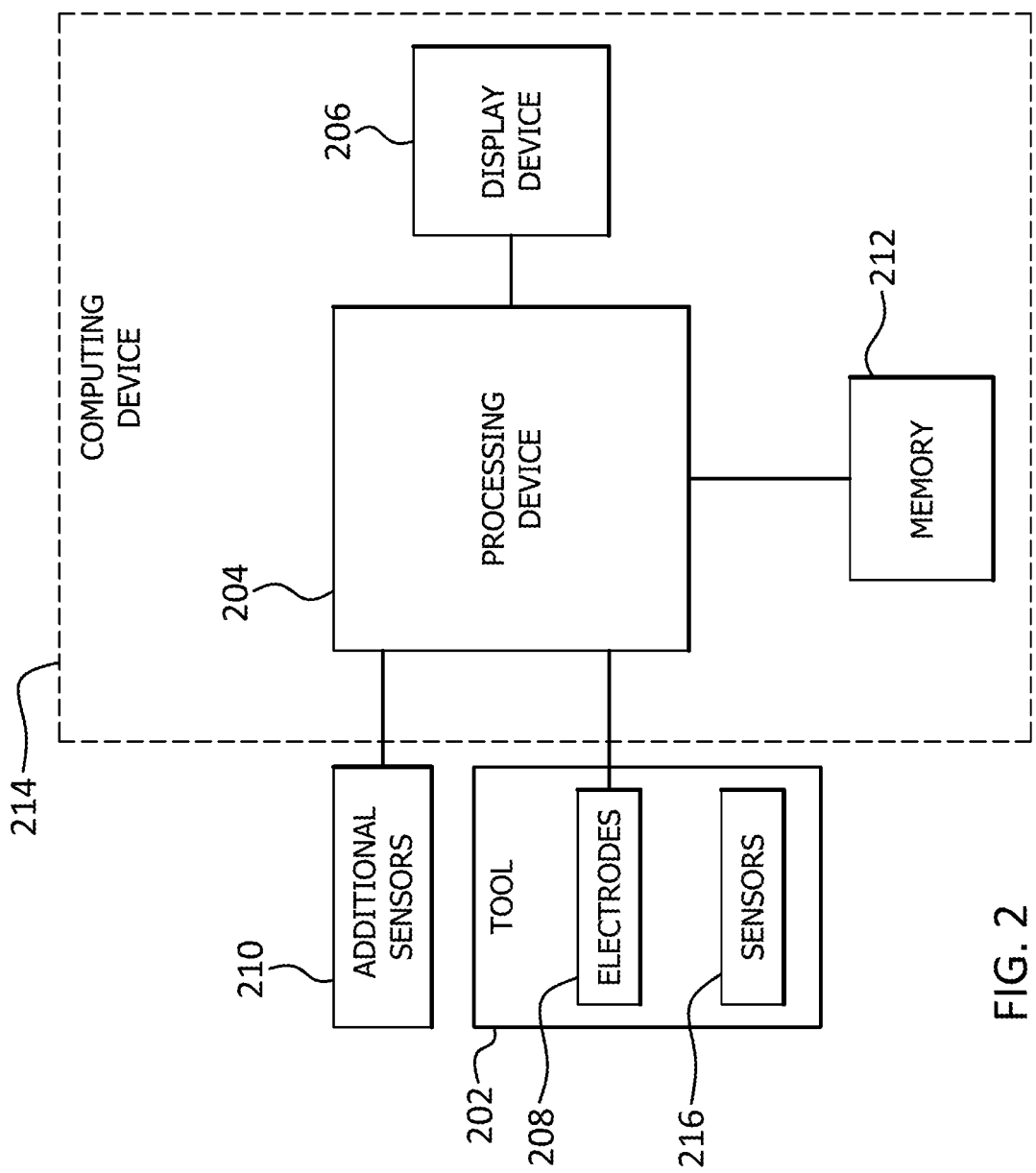
FIG. 2 is an illustration of components of an example electromagnetic navigation system for use with embodiments described herein.

FIG. 2 is a block diagram illustrating example components of a medical system 200 for use with embodiments described herein. As shown in FIG. 2, the system 200 includes a medical tool 202, a processing device 204, a display device 206, memory 212. For explanation purposes, the medical tool 202 will be described herein as catheter 202. In some examples, catheter 202 is also configured to ablate tissue at locations engaged by the catheter 202. As shown in FIG. 2, the processing device 204, display device 206 and memory 212 are a part of an example computing device 214. In some embodiments, the display device 206 may be separate from computing device 214. Computing device 214 may also include an I/O interface, such as I/O interface 42 shown in FIG. 1.

As shown in FIG. 2, catheter 202 includes one or more sensors 216, which include, for example, a magnetic field location sensor (e.g., sensor 38 in FIG. 1) for providing location signals to indicate the 3D position coordinates of the catheter 202. Sensors 216 also include, for example, position sensors, pressure or force sensors, temperature sensors, impedance sensors or other sensors which provide signals indicating parameters values (e.g., catheter position stability, impedance and TPI) during the medical procedure. In some procedures, one or more additional sensors 210 that are separate from the catheter 202, as shown in example system 200, are also used to provide location signals.

The catheter 202 also includes electrodes 208 for acquiring electrical activity of a portion of patient anatomy (e.g., a heart) and mapping the electrical activity of the heart. Any number of electrodes 208 can be used to continuously acquire electrical signals over time from different areas of the portion of patient anatomy (e.g., the heart). Each electrical signal acquired by a corresponding electrode indicates the electrical activity at a location of the heart in a 3D space.

Memory 212 includes, for example, volatile and non-volatile memory, such as random access memory (RAM), dynamic RAM, or a cache. Memory 212 also includes, for example, storage, such as, fixed storage (e.g., a hard disk drive and a solid state drive) and removable storage (e.g., an optical disk and a flash drive).

Catheter 202 is configured to be navigated within the patient anatomy, during a medical procedure, such that the electrodes 208 become in contact with or in close proximity to the heart. The acquired electrical signals are monitored and used, along with location information (e.g., acquired via sensors 216) indicating locations of the catheter 202 and the electrodes 208 in the 3D space, to create the dynamic maps of the heart. Catheter 202 may be in wired or wireless communication with processing device 204 to communicate the information acquired by sensors 216 and the electrical activity acquired by the electrodes 208.

Display device 206 is configured to display one or more maps of the heart in the 3D space including data corresponding to the acquired electrical signals (i.e., electrical signal data) of the portion of patient anatomy (e.g., the heart). For example, display device 206 is configured to display maps representing a spatio-temporal manifestation of the heart as well as the electrical signal data at regions of the heart on the maps. Display device 206 may be in wired or wireless communication with processing device 204. In some embodiments, display device may be separate from computing device 214. Display device 206 may include one or more displays each configured to display one or more maps.

Processing device 204 is configured to processes the acquired electrical signals (e.g., from electrodes 208) as electrical signal data and store, in memory 212, the electrical signal data acquired via electrodes 208. Processing device 204 is also configured to filter the acquired electrical signal data according to one or more filter parameter settings, generate mapping information and drive display device 206 to display the maps using the mapping information.

Filter parameter settings include, for example, a LAT range of the electrical signals, an electrical signal cycle length range, a position stability range of a medical tool used to navigate within the 3D space, a minimum force threshold of the medical tool, a maximum force threshold of the medical tool, a pacing density, an impedance value and a TPI.

For example, during a medical procedure, processing device 204 is configured to filter the electrical signal data according to filter parameter settings (e.g., first filter parameter settings) which are determined prior to the medical procedure (e.g., a hard filter) and generate first mapping information for displaying a map of the portion of patient anatomy (e.g., the heart) and the filtered electrical signal data. Display device 206 then displays the map of the heart and the filtered electrical signal data using the first mapping information.

The processing device 204 is also configured to receive an indication of a region of the portion of patient anatomy (e.g., region of the heart) on the displayed map. For example, processing device 204 receives an indication (e.g., a user input) of a location (e.g., area) on the displayed map and identifies the region of the heart on the displayed map from the indicated location on the map.

Processing device 204 re-filters the filtered electrical signal data according to one or more additional filter parameter settings (e.g., second filter parameter settings) and generates, second mapping information for displaying, at the indicated region of the heart on the map, a portion of the electrical signal data previously filtered from display. The processing device 204 re-filters the filtered electrical signal data by retrieving, from memory, the stored electrical signal data missing from the identified region of the heart on the map and reusing the retrieved electrical signal data for display at the identified region. For example, if additional filter parameter settings include a changed LAT range having LAT values previously missing from the display. Processing device 204 generates second mapping information for displaying, at the indicated region of the heart on the map, the electrical signal data for each LAT in the changed LAT range.

Figure 3:
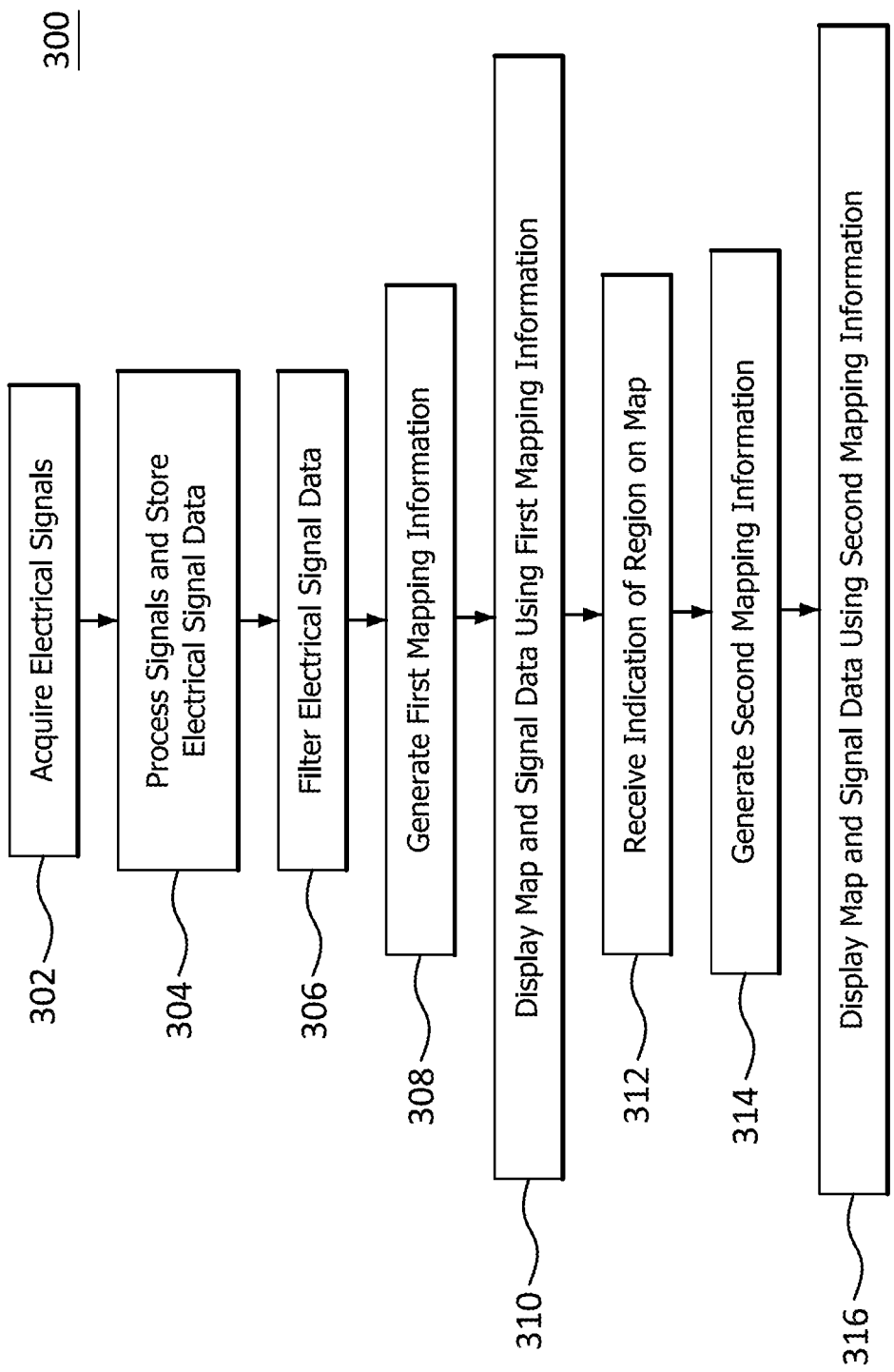
FIG. 3 is a flow diagram illustrating an example method of reusing electrical signal data acquired for a medical processing and display system according to embodiments described herein.

FIG. 3 is a flow diagram illustrating an example method 300 of reusing electrical signal data acquired for a medical processing and display system.

In the example method 300, the electrical signals represent the electrical activity of a heart. As shown at block 302, the method 300 includes acquiring electrical signals. For example, during a medical procedure, the electrical signals are acquired, over time, via a plurality of electrodes of a catheter navigated within the patient anatomy until the electrodes become in contact with or in close proximity to the heart. Each electrical signal is acquired via one of the sensors and each electrical signal indicates electrical activity at a location of a portion of the heart in a 3D space.

As shown at block 304, the method 300 includes processing the acquired electrical signals and storing the electrical signal data acquired via the electrodes over time. The electrical signals are processed (e.g., by processing device 204) as electrical signal data. For example, the electrical signal data may include a LAT of each acquired electrical signal and amplitude values for each acquired electrical signal. The electrical signal data may be continuously stored (e.g., in memory 212) over time during the medical procedure.

As shown at block 306, the method 300 includes filtering the electrical signal data according to a first plurality of filter parameter settings (e.g., filter parameter settings shown in FIGS. 6A and 6B). For example, the electrical signal data is filtered according to a first plurality of parameter settings which are determined prior to the medical procedure (e.g., a hard filter).

As shown at block 308, the method 300 includes generating mapping information (e.g., first mapping information). The first mapping information is generated, based on the first plurality of filter parameter settings, for displaying a map of the portion of the heart and the filtered electrical signal data. As shown at block 310, the method 300 includes displaying the map of the heart and the filtered electrical signal data based on the first mapping information.

Figure 4:
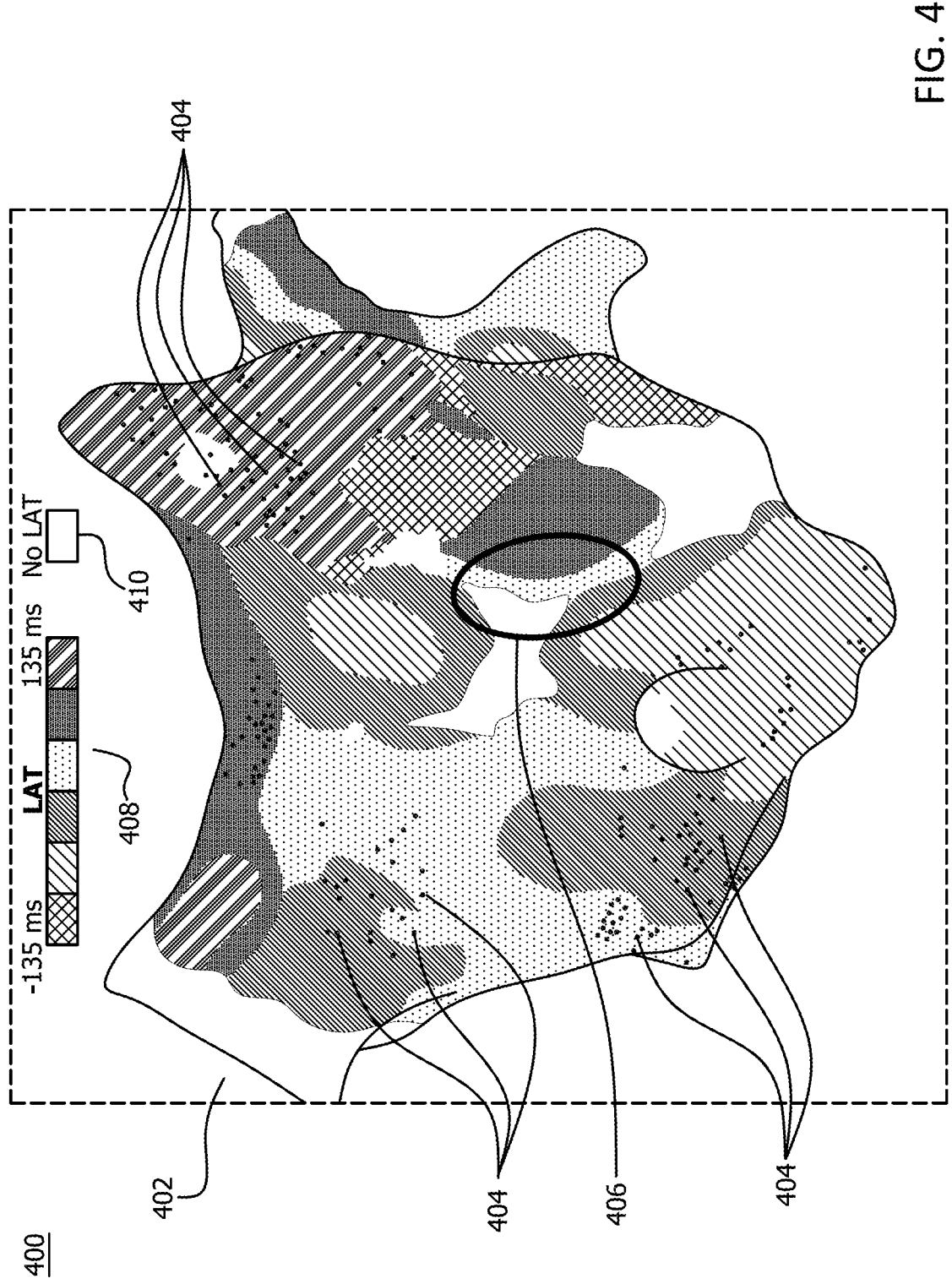
FIG. 4 is an example of a displayed map of a heart including electrical signal data points, at different regions of the heart, which have been filtered according to parameter settings.

FIG. 4 is an example of a map 400 of heart 402 including electrical signal data points 404 which are displayed according to the first mapping information. The broken lines around the map 400 are used to illustrate a display screen or a portion of a display screen. The electrical signal data points 404 are displayed at different regions of the heart 402 based on the first plurality of parameter settings. Each data point 404 represents a LAT of the electrical activity of the heart 402 acquired by one of the electrodes. As shown in FIG. 4, multiple LAT ranges are displayed at different regions of the heart 402. Each LAT range is displayed on a region of the heart 402 via one of a plurality of different visual indicators. Examples of visual indicators include colors, shadings or any other types of visual indicators having distinguishing visual features. FIG. 4 also includes bar legend 408 in which each visual indicator (e.g., color) on the legend 408 corresponds to one of the multiple LAT ranges between the lower and upper reference times of −135 ms and +135 ms. The reference times shown in FIG. 4 are merely an example of reference times. The reference times are set such that the time difference between the lower and upper reference times (e.g., between −135 ms and +135 ms=total of 270 ms) is approximately equal to the cycle length of the mapped chamber of the heart 402. Each LAT value (e.g., +70 ms) represents a difference in time between the LAT and a zero reference point of the cycle. An indicator, such as bar 410 in FIG. 4 may also be displayed to indicate regions in which no LAT range is displayed on the map 400.

As shown in FIG. 4, based on the first parameter settings, data points are not displayed at the region marked by the circle 406. For example, electrical signal data, corresponding to electrical signals acquired in the region 406 (marked by the circle shown in FIG. 4), may be missing because LATs of the electrical signals in region 406 occurred during a LAT time period range (e.g., between 68 ms and 70 ms from the zero reference point) and the first plurality of parameter settings filtered out LATs of the electrical signals occurring during the LAT range between 68 ms and 70 ms.

As shown at block 312, the method 300 includes receiving an indication of a region of the portion of patient anatomy on the map. For example, after viewing the map of the heart and the electrical signal data on the display device 206, medical personnel (e.g., a physician) may specify a region of the map, such as region 406 shown in FIG. 4. The configuration (e.g., size and shape) of region 406 shown in FIG. 4 is merely an example. In addition, the location of region 406 shown in FIG. 4 is also an example. Regions may be indicated as having and size and shape and be located at any region of the heart on the map. A region may be indicated, for example, via lines or shapes (e.g., circle shown in FIG. 4) on the display (e.g., a touch screen display). A size and shape of a region may also be predefined such that, in response to receiving an indication of a location on the display, the predefined size and shape of the region is identified at the indicated location.

As shown at blocks 314 and 316, the method 300 includes generating additional mapping information (e.g., second mapping information) and displaying the map of the heart and the filtered electrical signal data based on the second mapping information. The second mapping information is generated, based on one or more additional filter parameter settings (e.g., second filter parameter settings), for displaying a portion of the previously filtered data at the region on the map. The additional filter parameter settings also include, for example, a LAT range of the electrical signals, an electrical signal cycle length range, a position stability range of a medical tool used to navigate within the 3D space, a minimum force threshold of the medical tool, a maximum force threshold of the medical tool, a pacing density, an impedance value and a TPI.

Figure 5:
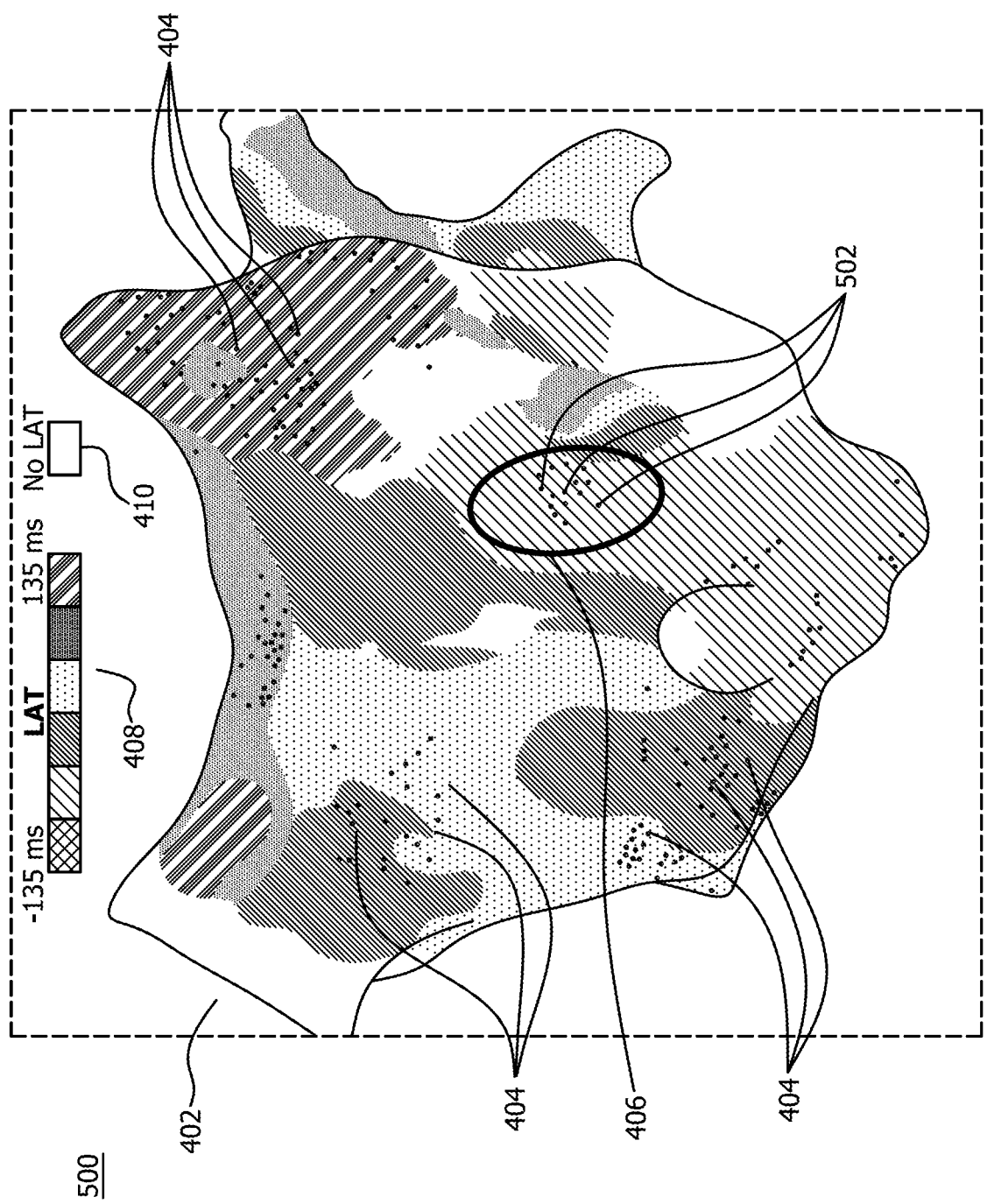
FIG. 5 is an example of a displayed map of the heart shown in FIG. 4 including new electrical signal data points, displayed at an indicated region of the heart, which have been filtered according to additional filter parameter settings.

FIG. 5 is an example of a displayed map 500 of the heart 402 shown in FIG. 4 including new electrical signal data points 502, displayed at the indicated region 406 of the heart 402, which have been filtered according to additional filter parameter settings (e.g., second filter parameter settings). The broken lines around the map 500 are used to illustrate a display screen or a portion of a display screen. In response to receiving the indication of the region 406 on the map 400 shown in FIG. 4, the region 406 is identified (e.g., by processing device 204) and the electrical signal data is re-filtered according to the second filter parameter settings by reusing stored electrical signal data that was previously filtered according to the first plurality of filter parameter settings.

In addition to indicating the region 406, the physician may also indicate a change to one or more filter parameters, such as a new LAT range to provide the electrical signal data missing from the indicated region. For example, in response to receiving an indication of region 406, a plurality of changeable filter parameter settings may be displayed. FIGS. 6A and 6B show examples of displayed changeable filter parameter settings. Upon viewing the changeable filter parameter settings, medical personnel, such as a physician, may change one or more of the parameter settings. For example, the physician may change the LAT range for the acquired electrical signals. In response to receiving the indication (e.g., user input) of the changed LAT range, additional second mapping information is generated to display each electrical signal data point acquired in the indicated region 406 within the defined LAT range. For example, as shown in FIG. 5, based on the second mapping information, new electrical signal data points 502 are displayed in the map 500 by retrieving the stored missing data points.

Alternatively, in response to receiving the indication of region 406, one or more filter parameters may be changed without receiving a user input (e.g., by the physician) indicating a change to a filter parameter. For example, in response to receiving the indication of region 406, the LAT range may be changed (e.g., increased from a LAT range set by the first parameter settings) to a second predetermined LAT range and second mapping information is generated, which results in the display of the electrical signal data points acquired in the indicated region 406.

The physician may also change filter parameter settings for one or more filter parameters after viewing the displayed map which is re-filtered according to the second filter parameter settings (i.e., the re-filtered map 500). For example, after viewing the re-filtered displayed map 500, the physician may also change additional parameter settings for one or more regions of the map.

Different filter parameter settings may also be defined (e.g., by the physician) for regions of a portion of patient anatomy (e.g., the heart). Filter parameter settings may be specified for regions of the map according to the characteristics of the regions.

Figure 6C:
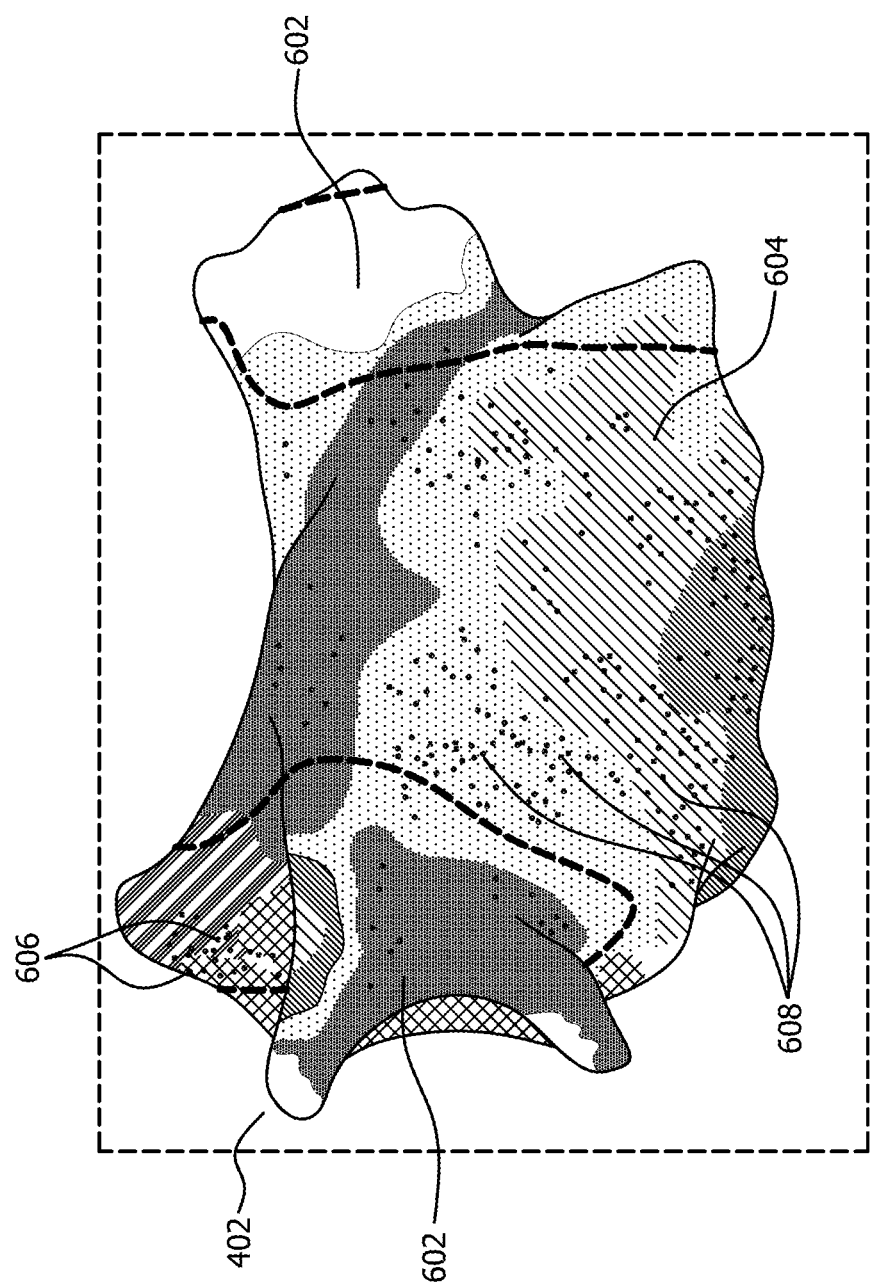
FIG. 6C illustrates an example of a displayed map of a heart including data displayed at the pulmonary vein regions of the heart according to the filter parameter settings shown in FIG. 6A and data displayed at the central region according to the filter parameter settings shown in FIG. 6B.

FIGS. 6A-6C are used to illustrate examples of displaying electrical signal data points at different anatomical regions according to different filter parameter settings for the different regions. FIG. 6A is an example of displayed filter parameter settings for filtering data displayed in the pulmonary vein regions 602 of the heart 402 shown in FIG. 6C. The filter parameter settings shown in FIG. 6A include a first setting (e.g., 3 mm) for a position stability parameter 610. FIG. 6B is an example of displayed filter parameter settings for filtering data displayed in a central region 604 of the heart 402 shown in FIG. 6C. The filter parameter settings shown in FIG. 6B include a second setting (e.g., 1 mm) for the position stability parameter 610. FIG. 6C illustrates an example of a displayed map 600 of heart 402 including electrical signal data points 606 displayed at pulmonary vein regions 602 of the heart 402 according to the filter parameter settings shown in FIG. 6A and electrical signal data points 608 displayed at central region 604 according to the filter parameter settings shown in FIG. 6B.

The broken lines around the filter parameter settings in FIGS. 6A and 6B and around the map 600 in FIG. 6C are used to illustrate a display screen or a portion of a display screen. The broken lines on the heart 402 in FIG. 6C are used to indicate the separation between the central region 604 and the two pulmonary vein regions 602 on either side of the central region 604. The size and location of the regions 602 and 604 shown in FIG. 6C are merely an example. The number of regions shown in FIG. 6C are also merely an example. Examples may include any number of regions displayed according to different parameter filter settings.

Referring generally to FIGS. 6A-6C, a physician may, for example, encounter a region, such as the pulmonary vein regions 602 of the heart 402, where it is difficult to maintain stability of a position of a catheter. In this case, the physician may choose not to define a position stability filter setting for pulmonary vein regions 602, enabling the physician to acquire data points in regions 602 with little or no dependency on catheter position stability. The position stability filter setting (e.g., value) is, for example, a distance (e.g., in mm) which causes electrical signal data, acquired by the catheter (e.g., by an electrode of the catheter) at a current position (e.g., current location in the 3D space), to be filtered from display when a change in distance from a position of the catheter during a previous heartbeat and the current position of the catheter is equal to or greater than the set position stability distance.

For example, as shown in FIG. 6A, the position stability distance is set to 3 mm for the pulmonary vein regions 602 of the heart 402, where it is difficult to maintain stability of a position of a catheter. In this case, signals are acquired for the pulmonary vein regions 602 if the position of the catheter does not change by a distance of 3 mm or more. Data points may also be acquired in the pulmonary vein regions 602 with no dependency on catheter position stability (i.e., regardless of position stability), for example, by unchecking the box next to position stability. Alternatively, as shown in FIG. 6B, the position stability is set to 1 mm for the central regions 604 of the heart 402 where it is less difficult to maintain stability of a position of a catheter.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. A method of reusing data which improves processing performance of a medical display processing system, the method comprising:
   acquiring, electrical signals indicating electrical activity at a portion of patient anatomy;
   filtering electrical signal data, corresponding to the electrical signals, according to a first plurality of filter parameter settings;
   generating first mapping information for displaying a map of the portion of patient anatomy and the filtered electrical signal data on a display; and
   generating, second mapping information for displaying, at a region on the map, a portion of the electrical signal data previously filtered from the display.

2. The method of claim 1, wherein the portion of patient anatomy is a heart and the electrical signals are electro-cardiogram (ECG) signals.

3. The method of claim 1, wherein the filter parameter settings comprise at least one of a local activation time (LAT) range of the electrical signals, an electrical signal cycle length range, a position stability range of a medical tool used to navigate within a 3D space, a minimum force threshold of the medical tool, a maximum force threshold of the medical tool, a pacing density, an impedance and a tissue proximity indication (TPI).

4. The method of claim 1, further comprising storing the electrical signal data corresponding to the acquired electrical signals,
   wherein generating the second mapping information further comprises retrieving the portion of the stored electrical signal data corresponding to the acquired electrical signals.

5. The method of claim 1, further comprising:
   re-filtering the filtered electrical signal data according to a second plurality of filter parameter settings; and
   generating the second mapping information for displaying the re-filtered electrical signal data at the region indicated on the map.

6. The method of claim 5, further comprising:
   receiving an indication to change at least one of the second plurality of filter parameter settings;
   re-filtering the electrical signal data a second time according to the at least one changed filter parameter setting; and
   generating, third mapping information for displaying, at the region indicated on the map, the electrical signal data that is re-filtered the second time.

7. The method of claim 1, further comprising receiving an indication of another region, different from the region, of the portion of patient anatomy on the map,
   wherein the second mapping information is generated for further displaying, at the other region on the map, the portion of the electrical signal data previously filtered from display according to the first plurality of filter parameter settings.

8. A medical display processing device which improves processing performance, the processing device comprising:
   memory configured to store electrical signal data; and
   a processing device configured to:
   receive the electrical signal data, corresponding to electrical signals acquired indicating electrical activity at a portion of patient anatomy;
   filter the electrical signal data according to a first plurality of filter parameter settings;
   generate first mapping information for displaying a map of the portion of patient anatomy and the filtered electrical signal data on a display; and
   generate, second mapping information for displaying, at a region on the map, a portion of the electrical signal data previously filtered from the display.

9. The processing device of claim 8, wherein the portion of patient anatomy is a heart and the electrical signals are electro-cardiogram (ECG) signals.

10. The processing device of claim 8, wherein the filter parameter settings comprise at least one of a local activation time (LAT) range of the electrical signals, an electrical signal cycle length range, a position stability range of a medical tool used to navigate within a 3D space, a minimum force threshold of the medical tool, a maximum force threshold of the medical tool, a pacing density, an impedance and a tissue proximity indication (TPI).

11. The processing device of claim 8, wherein the processing device is further configured to store, in the memory, the electrical signal data corresponding to the acquired electrical signals,
   generate the second mapping information by retrieving the portion of the stored electrical signal data corresponding to the acquired electrical signals.

12. The processing device of claim 8, wherein the processing device is further configured to:
   re-filter the filtered electrical signal data according to a second plurality of filter parameter settings; and
   generate the second mapping information for displaying, at the region indicated on the map, the re-filtered electrical signal data.

13. The processing device of claim 12, wherein the processing device is further configured to:
   receive an indication to change at least one of the second plurality of filter parameter settings;
   re-filter the electrical signal data a second time according to the at least one changed filter parameter setting; and
   generate, third mapping information for displaying, at the region indicated on the map, the electrical signal data that is re-filtered the second time.

14. The processing device of claim 8, wherein the processing device is further configured to:
   receive an indication of another region, different from the region, of the portion of patient anatomy on the map,
   wherein the second mapping information is generated for further displaying, at the other region on the map, the portion of the electrical signal data previously filtered from display according to the first plurality of filter parameter settings.

15. A medical processing system which improves processing performance, the system comprising:
a plurality of electrodes each configured to acquire electrical signals indicating electrical activity at a portion of patient anatomy;
a display device configured to display a map of the portion of patient anatomy and electrical signal data corresponding to the electrical signals; and
a processing device configured to:
receive the electrical signal data;
filter the electrical signal data according to a first plurality of filter parameter settings;
generate first mapping information for displaying, on the display device, the map of the portion of patient anatomy and the filtered electrical signal data; and
generate, second mapping information for displaying, on the display device at a region on the map, a portion of the electrical signal data previously filtered from the display device.

16. The system of claim 15, further comprising a medical tool configured to navigate within the patient anatomy and comprising the plurality of electrodes.

17. The system of claim 15, wherein the portion of patient anatomy is a heart and the electrical signals are electrocardiogram (ECG) signals.

18. The system of claim 15, wherein the processing device is further configured to:
re-filter the filtered electrical signal data according to a second plurality of filter parameter settings; and
generate the second mapping information for displaying, at the region indicated on the map, the re-filtered electrical signal data.

19. The system of claim 18, wherein the processing device is further configured to:
receive an indication to change at least one of the second plurality of filter parameter settings;
re-filter the electrical signal data a second time according to the at least one changed filter parameter setting; and
generate, third mapping information for displaying, at the region indicated on the map, the electrical signal data that is re-filtered the second time.

20. The system of claim 15, wherein the processing device is further configured to:
receive an indication of another region, different from the region, of the portion of patient anatomy on the map, wherein the second mapping information is generated for further displaying, at the other region on the map, the portion of the electrical signal data previously filtered from display according to the first plurality of filter parameter settings.

* * * * *